(12) United States Patent
Souleymanou et al.

(10) Patent No.: US 10,421,735 B2
(45) Date of Patent: *Sep. 24, 2019

(54) METHOD FOR PRODUCING 5-HYDROXYMETHYLFURFURAL IN THE PRESENCE OF CATALYSTS OF THE FAMILY OF HOMOGENEOUS SULFONIC ACIDS IN THE PRESENCE OF AT LEAST ONE APROTIC POLAR SOLVENT

(71) Applicant: IFP Energies nouvelles, Rueil-Malmaison (FR)

(72) Inventors: Myriam Souleymanou, Neuilly Plaisance (FR); Marc Jacquin, Lyons (FR); Damien Delcroix, St. Maurice L Exil (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/773,036

(22) PCT Filed: Oct. 17, 2016

(86) PCT No.: PCT/EP2016/074902
§ 371 (c)(1),
(2) Date: May 2, 2018

(87) PCT Pub. No.: WO2017/076626
PCT Pub. Date: May 11, 2017

(65) Prior Publication Data
US 2018/0319760 A1 Nov. 8, 2018

(30) Foreign Application Priority Data
Nov. 2, 2015 (FR) .................... 15 60460

(51) Int. Cl.
*C07D 307/02* (2006.01)
*C07D 307/50* (2006.01)
*C07D 307/46* (2006.01)

(52) U.S. Cl.
CPC ......... *C07D 307/50* (2013.01); *C07D 307/46* (2013.01)

(58) Field of Classification Search
CPC ..................................... C07D 307/50
USPC .......................................... 549/488
See application file for complete search history.

(56) References Cited

U.S. PATENT DOCUMENTS

2008/0033187 A1  2/2008 Zhao

FOREIGN PATENT DOCUMENTS

WO     2006063220 A2    6/2006

OTHER PUBLICATIONS

International Search Report PCT/EP2016/074902 dated Nov. 18, 2016.
Kawamoto et al: "Inhibition of acid-catalyzed depolymerization of cellulose with boric acid in non-aqueous acidic media", Carbohydrate Research, Pergamon, GB, vol. 343, No. 2, Nov. 7, 2007 (Nov. 7, 2007), pp. 249-255.
Héctor Quiroz-Florentino et al: "Total synthesis of the natural succinate derivative of 5-(hydroxymethyl) furfural isolated from the Noni fruit (*Morinda citrifolia*)", Natural Product Research, vol. 23, No. 14, Sep. 20, 2009 (Sep. 20, 2009), GB, pp. 1355-1362.

*Primary Examiner* — Taylor V Oh
(74) *Attorney, Agent, or Firm* — Millen, White, Zelano and Branigan, P.C.

(57) ABSTRACT

The invention relates to a novel process for the conversion of a feedstock comprising at least one sugar to 5-hydroxymethylfurfural, in which said feedstock is contacted with one or more catalysts of the family of the homogeneous sulphonic acids in the presence of at least one aprotic polar solvent, used alone or in a mixture, at a temperature comprised between 30° C. and 200° C., and at a pressure comprised between 0.1 MPa and 10 MPa in which said catalysts are selected from the compounds of general formula

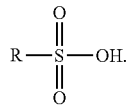

12 Claims, No Drawings

METHOD FOR PRODUCING 5-HYDROXYMETHYLFURFURAL IN THE PRESENCE OF CATALYSTS OF THE FAMILY OF HOMOGENEOUS SULFONIC ACIDS IN THE PRESENCE OF AT LEAST ONE APROTIC POLAR SOLVENT

TECHNICAL FIELD OF THE INVENTION

The invention relates to a process for the conversion of sugars and in particular hexoses to 5-hydroxymethylfurfural in the presence of catalysts of the family of the homogeneous sulphonic acids in the presence of at least one aprotic polar solvent.

PRIOR ART 5-hydroxymethylfurfural (5-HMF) is a compound derived from biomass which can be reused in many fields as a precursor of active ingredients in pharmacy, agricultural chemistry or specialist chemicals. During the last few years, it has been used to advantage as a precursor of furandicarboxylic acid (FDCA), which is used as a substitute for terephthalic acid as a monomer for the production of polyester fibres or consumer plastics.

The production of 5-HMF by the dehydration of hexoses has been known for many years and has been the subject of a significant number of research studies. On the one hand, the dehydration of glucose or fructose to 5-HMF is described in an aprotic polar solvent, for example dimethyl sulphoxide DMSO or N-methyl-pyrrolidone NMP, in the presence of a heterogeneous acid catalyst, i.e. supported catalysts that are insoluble in the reaction medium such as the sulphonic silicas described by Bao et al., Catal. Commun. 2008, 9, 1383, with performances corresponding to yields of 5-HMF of approximately 70%. On the other hand, the dehydration of glucose or fructose to 5-HMF is described, for example in patent applications US 2014/0235881, US 2014/0357878 and US 2015/0045576 in a protic polar solvent, for example water or ethanol, in the presence of heterogeneous or homogeneous acid catalysts, i.e. the latter are soluble in the reaction medium, with the production of by-products of the family of the carboxylic acids, esters and ethers such as levulinic acid and esters thereof, formic acid and esters thereof as well as alkoxylated derivatives of 5-HMF such as 5-ethoxymethylfurfural. Obtaining these products requires costly additional separation and purification steps, impacting the financial profitability of the process.

Thus, there is a need for the development of new processes for the selective conversion of sugars to 5-HMF making it possible to obtain improved yields, while limiting the production of unwanted by-products.

Surprisingly, the applicant has demonstrated that contacting sugars with one or more catalysts of the family of the homogeneous sulphonic acids in the presence of at least one aprotic polar solvent made it possible to significantly increase the yields of 5-HMF, while limiting the production of unwanted by-products.

Thus, the invention relates to a process for the production of 5-hydroxymethylfurfural from sugars using catalysts of the family of the homogeneous sulphonic acids in the presence of at least one aprotic polar solvent.

Subject of the Invention

A subject of the present invention is therefore to provide a novel process for the conversion of a feedstock comprising at least one sugar to 5-hydroxymethylfurfural, in which said feedstock is contacted with one or more catalysts of the family of the homogeneous sulphonic acids in the presence of at least one aprotic polar solvent, used alone or in a mixture, at a temperature comprised between 30° C. and 200° C., and at a pressure comprised between 0.1 MPa and 10 MPa in which said catalysts are selected from the compounds of general formula

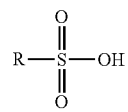

in which R is selected from the halogen groups, the alkyl groups, linear or branched, cyclic or non-cyclic, comprising 1 to 20 carbon atoms being able to be substituted or not with at least one substituent selected from:

the oxo group, the halogen groups and, the aryl groups, fused or not, being able to be substituted or not with halogen groups and/or linear or branched, cyclic or non-cyclic alkyl groups comprising 1 to 20 carbon atoms, the aryl groups comprising 6 to 14 carbon atoms being able to be substituted or not with at least one substituent selected from:

the alkyl groups, linear or branched, cyclic or non-cyclic, comprising 1 to 20 carbon atoms, being able to be substituted or not with at least one halogenated group or at least one nitro group, the halogenated groups and, the nitro group.

By catalyst of the family of the sulphonic acids is meant a molecule of the family of the sulphonic acids bearing an $SO_3H$ acid function.

By homogeneous sulphonic acid is meant a sulphonic acid that is soluble in the reaction medium.

By aprotic solvent is meant a molecule acting as a solvent, all the hydrogens of which are borne by carbon atoms.

By polar solvent is meant a molecule acting as a solvent, the dipole moment μ of which expressed in Debye has a numerical value greater than or equal to 2.00 measured at 25° C.

Thus, by aprotic polar solvent is meant a molecule acting as a solvent, all the hydrogens of which are borne by carbon atoms, and the dipole moment μ of which expressed in Debye has a numerical value greater than or equal to 2.00 measured at 25° C.

An advantage of the present invention is to provide a process for the conversion of sugars to 5-hydroxymethylfurfural using one or more catalysts of the family of the homogeneous sulphonic acids in aprotic polar solvents, while limiting the production of unwanted by-products such as products of the family of the carboxylic acids, esters, ethers and humins. The humins are secondary condensation products resulting from the degradation of the sugars in an acid medium such as polyfurans.

DETAILED DESCRIPTION OF THE INVENTION

The Feedstock

The feedstock treated in the process according to the invention is a feedstock comprising at least one sugar, preferably selected from the oligosaccharides and the monosaccharides, alone or in a mixture.

By sugar is meant any oligosaccharide or monosaccharide soluble in the reaction conditions envisaged by the invention.

By monosaccharide is meant more particularly the carbohydrates of general formula $C_6(H_2O)_6$ or $C_6H_{12}O_6$. The preferred monosaccharides used as feedstock in the present invention are selected from glucose, mannose and fructose, used alone or in a mixture.

By oligosaccharide is meant more particularly a carbohydrate having the empirical formula $C_{6n}H_{10n+2}O_{5n+1}$ where n is an integer greater than 1, the monosaccharide units composing said oligosaccharide being identical or not, and/or a carbohydrate having the empirical formula $(C_{6m}H_{10m+2}O_{5m+1})(C_{5n}H_{8n+2}O_{4n+1})$ where m and n are integers greater than or equal to 1, the monosaccharide units composing said oligosaccharide being identical or not.

The oligosaccharides are preferably selected from the oligomers of hexoses or pentoses and hexoses, preferably from the oligomers of hexoses, preferably with a degree of polymerization allowing them to be soluble under the reaction conditions envisaged by the invention. They can be obtained by partial hydrolysis of polysaccharides originating from renewable resources such as starch, inulin, cellulose or hemicellulose, optionally originating from lignocellosic biomass. For example, steam explosion of lignocellosic biomass is a process of partial hydrolysis of the cellulose and hemicellulose contained in the lignocellosic biomass producing a flow of oligo- and monosaccharides.

The preferred oligosaccharides used as feedstock in the present invention are preferably selected from saccharose, lactose, maltose, isomaltose, inulobiose, melibiose, gentiobiose, trehalose, cellobiose, cellotriose, cellotetraose and the oligosaccharides originating from the hydrolysis of said polysaccharides originating from the hydrolysis of starch, inulin, cellulose or hemicellulose, used alone or in a mixture.

Preferably, the feedstock comprising at least one sugar used in the process according to the invention is selected from cellobiose, fructose and glucose, used alone or in a mixture.

Very preferably, said feedstock is selected from fructose and glucose, used alone or in a mixture.

The Catalysts

According to the invention, said feedstock is contacted in the process according to the invention with at least one catalyst of the family of the homogeneous sulphonic acids in the presence of at least one aprotic polar solvent used alone or in a mixture, at a temperature comprised between 30° C. and 200° C., and at a pressure comprised between 0.1 MPa and 10 MPa.

According to the invention, the catalyst is selected from the homogeneous sulphonic acid compounds of general formula:

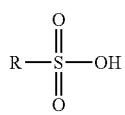

in which R is selected from
the halogen groups,
the alkyl groups, linear or branched, cyclic or non-cyclic, comprising 1 to 20 carbon atoms being able to be substituted or not with at least one substituent selected from:
the oxo group,
the halogen groups and,
the aryl groups, fused or not, being able to be substituted or not with halogen groups and/or linear or branched, cyclic or non-cyclic alkyl groups comprising 1 to 20 carbon atoms,
the aryl groups comprise 6 to 14 carbon atoms being able to be substituted or not with at least one substituent selected from:
the alkyl groups, linear or branched, cyclic or non-cyclic, comprising 1 to 20 carbon atoms, being able to be substituted or not with at least one halogenated group or at least one nitro group,
the halogenated groups and,
the nitro group.

In the case where R is a halogen group, said halogen group is preferably selected from fluorine, chlorine, bromine and iodine.

Preferably, in the case where R is a halogen group, said halogen group is fluorine.

In the case where R is a linear alkyl group, said linear alkyl group contains 1 to 20 carbon atoms, preferably 1 to 10 carbon atoms and more preferably 1 to 6 carbon atoms.

Even more preferably, in the case where R is a linear alkyl group, said linear alkyl group is selected from the methyl, ethyl and propyl groups.

Very advantageously, in the case where R is a linear alkyl group, said linear alkyl group is methyl and the catalyst of the family of the sulphonic acids is methanesulphonic acid.

In the case where R is a branched alkyl group, said branched alkyl group contains 3 to 20 carbon atoms, preferably 3 to 10 carbon atoms and more preferably 3 to 6 carbon atoms.

Even more preferably, in the case where R is a branched alkyl group, said branched alkyl group is selected from the isopropyl, isobutyl and tertbutyl groups.

In the case where R is a cyclic alkyl group, said cyclic alkyl group contains 3 to 20 carbon atoms, preferably 5 to 8 carbon atoms.

Preferably, in the case where R is a cyclic alkyl group, said cyclic alkyl group is selected from the cyclopentyl and cyclohexyl groups.

In the case where R is an alkyl group substituted with at least one oxo ($=O$) group said oxo group can be positioned on a terminal carbon or not. Said oxo group thus being able to form part of a ketone, aldehyde or carboxylic acid function.

Preferably, in the case where R is an alkyl group substituted with at least one oxo ($=O$) group said oxo group forms part of a ketone or aldehyde function.

In the case where R is an alkyl group substituted with at least one halogen group, said halogen group is preferably selected from fluorine, chlorine, bromine and iodine and preferably fluorine.

Very preferably, in the case where R is an alkyl group substituted with at least one halogen group, R is trifluoromethyl and the catalyst of the family of the sulphonic acids is trifluoromethanesulphonic acid.

In the case where R is an alkyl group substituted with at least one aryl group, said aryl group is advantageously selected from phenyl, tolyl and naphthyl.

Preferably, in the case where R is an alkyl group substituted with at least one aryl group, said aryl group is the phenyl and R is the benzyl group.

In the case where R is an alkyl group substituted with at least one aryl group, said alkyl group is advantageously substituted by at least one halogen group selected from fluorine, chlorine, bromine and iodine, preferably fluorine.

In the case where R is an aryl group, said aryl group contains 6 to 14 carbon atoms, preferably 6 to 10 carbon atoms.

Preferably, in the case where R is an aryl group, said aryl group is phenyl or naphthyl.

In the case where R is an aryl group substituted with at least one halogen group, said halogen group is preferably selected from fluorine, chlorine, bromine and iodine and preferably fluorine.

In the case where R is an aryl group substituted with at least one alkyl group, said alkyl group is advantageously selected from the linear or branched alkyls containing 1 to 6 carbon atoms.

Preferably, in the case where R is an aryl group substituted with at least one alkyl group, said alkyl group is selected from methyl, ethyl, propyl and isopropyl.

Even more preferably, in the case where R is an aryl group substituted with at least one alkyl group, said alkyl group is methyl and the catalyst of the family of the sulphonic acids is paratoluenesulphonic acid.

In the case where R is an aryl group substituted with an alkyl group, said alkyl group is advantageously substituted by at least one halogen group selected from fluorine, chlorine, bromine and iodine, preferably fluorine.

Conversion Process

According to the invention, the process for the conversion of the feedstock comprising at least one sugar is implemented in a reaction chamber in the presence of at least one solvent, said solvent being an aprotic polar solvent or a mixture of aprotic polar solvents, at a temperature comprised between 30° C. and 200° C., and at a pressure comprised between 0.1 MPa and 10 MPa.

The process is thus implemented in a reaction chamber comprising at least one aprotic polar solvent and in which said feedstock is placed in the presence of at least one catalyst of the family of the sulphonic acids according to the invention.

According to the invention, the process takes place in the presence of at least one solvent, said solvent being an aprotic polar solvent or a mixture of aprotic polar solvents.

The aprotic polar solvents are advantageously selected from all the aprotic polar solvents the dipole moment of which expressed in Debye (D) is greater than or equal to 2.00. Preferably, the aprotic polar solvents are selected from pyridine (2.37), butan-2-one (5.22), acetone (2.86), acetic anhydride (2.82), N,N,N',N'-tetramethylurea (3.48), benzonitrile (4.05), acetonitrile (3.45), methyl ethyl ketone (2.76), propionitrile (3.57), hexamethylphosphoramide (5.55), nitrobenzene (4.02), nitromethane (3.57), N,N-dimethylformamide (3.87), N,N-dimethylacetamide (3.72), sulpholane (4.80), N-methylpyrrolidone (4.09), dimethyl sulphoxide (3.90), propylene carbonate (4.94) and γ-valerolactone (4.71) alone or in a mixture.

Preferably, the aprotic polar solvents are advantageously selected from acetone, N,N-dimethylformamide, N,N-dimethylacetamide, sulpholane, N-methylpyrrolidone, dimethyl sulphoxide, propylene carbonate and γ-valerolactone alone or in a mixture.

Preferably, the aprotic polar solvents are advantageously selected from N,N-dimethylacetamide, N-methylpyrrolidone, dimethyl sulphoxide and γ-valerolactone alone or in a mixture.

Preferably, said process according to the invention takes place at a temperature comprised between 50° C. and 200° C. and preferably between 50° C. and 175° C., and at a pressure comprised between 0.1 MPa and 8 MPa and preferably between 0.1 and 5 MPa.

Generally, the method can be carried out according to different embodiments. Thus, the process can advantageously be carried out in batches or continuously. It can take place in a closed reactor chamber or in a semi-open reactor.

The catalyst or catalysts of the family of the homogeneous sulphonic acids are introduced into the reactor chamber at the rate of a quantity corresponding to a feedstock/catalyst(s) mass ratio comprised between 1 and 1000, preferably between 1 and 500, preferably between 1 and 200, preferably between 1 and 150.

The feedstock is introduced into the process at the rate of a quantity corresponding to a solvent/feedstock mass ratio comprised between 0.1 and 200, preferably between 0.3 and 100 and even more preferentially between 1 and 50.

If a continuous process is selected, the mass hourly velocity (mass flow of feedstock/weight of catalyst(s)) is comprised between 0.01 $h^{-1}$ et 5 $h^{-1}$, preferably between 0.02 $h^{-1}$ et 2 $h^{-1}$.

At the end of the reaction, the catalyst can easily be recovered by precipitation, distillation, extraction or washing. It can also be recovered by passing it though an ion exchange resin such as Amberlyst 31 and recycled after washing of this resin.

Products Obtained and Method of Analysis Thereof

The product of the reaction of the conversion process according to the invention is 5-hydroxymethylfurfural (5-HMF).

At the end of the reaction, the reaction medium is analyzed by gas chromatography (GC) in order to determine the 5-HMF content in the presence of an internal standard and by ionic chromatography in order to determine the conversion of the feedstock in the presence of an external standard and in order to quantify the unwanted products such as levulinic acid, formic acid, alkoxymethylfurfural and humins.

EXAMPLES

In the examples below, the glucose and fructose used as feedstock are commercial and are used without additional purification.

The Amberlyst 15 and methanesulphonic acid denoted MSA in the examples are commercial and used without additional purification.

The dimethyl sulphoxide, denoted DMSO in the examples and the N-methylpyrrolidone, denoted NMP in the examples, used as aprotic polar solvents, are commercial and used without additional purification.

The ethanol used as a protic polar solvent is commercial and used without additional purification.

For Examples 1 to 8 of the conversion of sugars to 5-HMF, the molar yield of 5-HMF is calculated using the ratio between the number of moles of 5-HMF obtained and the number of moles of sugar feedstock used.

Example 1

Conversion of Fructose Utilizing Methanesulphonic Acid in NMP (According to the Invention)

Methanesulphonic acid (0.018 g, 0.19 mmol) is added to a solution of fructose (2.0 g, 11.10 mmol) in NMP (20 g). The feedstock/catalyst mass ratio is 111. The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is 78%. The yield of unwanted humins is 22%.

Example 2

Conversion of a Mixture of Glucose and Fructose Utilizing Methanesulphonic Acid in NMP (According to the Invention)

Methanesulphonic acid (0.018 g, 0.19 mmol) is added to a mixture of fructose and glucose 50% by weight/50% by weight (2.0 g, 11.10 mmol) in NMP (20 g). The feedstock/catalyst mass ratio is 111. The solvent/feedstock mass ratio is 10. The reaction medium is then stirred at 120° C. for 6 h. The conversion of the mixture of fructose and glucose to 5-HMF is monitored by regular sampling of an aliquot of solution which is immediately cooled to 0° C., redissolved in water and tested by ionic chromatography. The molar yield of 5-HMF after 6 h is 70%. The yield of unwanted humins is 30%.

Example 3

Conversion of Fructose Utilizing Methanesulphonic Acid in DMSO (According to the Invention)

Methanesulphonic acid (0.018 g, 0.19 mmol) is added to a solution of fructose (2.0 g, 11.10 mmol) in DMSO (20 g). The feedstock/catalyst mass ratio is 111. The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is 82%. The yield of unwanted humins is 18%.

Example 4

Conversion of a Mixture of Glucose and Fructose Utilizing Methanesulphonic Acid in DMSO (According to the Invention)

Methanesulphonic Acid (0.018 g, 0.19 mmol) is added to a mixture of fructose and glucose 50% by weight/50% by weight (2.0 g, 11.10 mmol) in DMSO (20 g). The feedstock/catalyst mass ratio is 111. The solvent/feedstock mass ratio is 10. The reaction medium is then stirred at 120° C. for 6 h. The conversion of the mixture of fructose and glucose to 5-HMF is monitored by regular sampling of an aliquot of solution which is immediately cooled to 0° C., redissolved in water and tested by ionic chromatography. The molar yield of 5-HMF after 6 h is 76%. The yield of unwanted humins is 24%.

Comparative Example 5

Conversion of Fructose without Catalyst in NMP (not According to the Invention)

Fructose (2.0 g, 11.10 mmol) is dissolved in NMP (20 g). The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is less than 1%. The yield of unwanted humins is 40%.

Comparative Example 6

Conversion of Fructose without Catalyst in DMSO (not According to the Invention)

Fructose (2.0 g, 11.10 mmol) is dissolved in DMSO (20 g). The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is 65%. The yield of unwanted humins is 35%.

Comparative Example 7

Conversion of Fructose Utilizing a Heterogeneous Sulphonic Acid Catalyst Amberlyst 15 in NMP (not According to the Invention)

Amberlyst 15 (0.040 g, 0.19 mmol) is added to a solution of fructose (2.0 g, 11.10 mmol) in NMP (20 g). The feedstock/catalyst mass ratio is 50. The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is 45%. The yield of unwanted humins is 55%.

Comparative Example 8

Conversion of Fructose Utilizing Methanesulphonic Acid in Ethanol, Protic Polar Solvent (not According to the Invention)

Methanesulphonic acid (0.018 g, 0.19 mmol) is added to a solution of fructose (2.0 g, 11.10 mmol) in ethanol (20 g). The feedstock/catalyst mass ratio is 111. The solvent/feedstock mass ratio is 10. The reaction medium is then stirred at 120° C. for 6 h. The conversion of fructose to 5-HMF is monitored by regular sampling of an aliquot of solution which is immediately cooled to 0° C., redissolved in water and tested by ionic chromatography. The molar yield of 5-HMF after 6 h is 17%. The yields of unwanted ethyl levulinate, 5-ethoxymethylfurfural and humins are 7%, 5% and 37% respectively.

The results showing the yield of 5-HMF during sampling carried out after reaction for 6 hours are summarized in Table 1.

TABLE 1

| Example | Feedstock | Catalyst | Solvent | Yield 5-HMF (%) | Yield unwanted products (%) |
|---|---|---|---|---|---|
| 1 (according to the invention) | Fructose | MSA | NMP | 78 | Humins 22 |
| 2 (according to the invention) | Glucose + Fructose | MSA | NMP | 70 | Humins 30 |
| 3 (according to the invention) | Fructose | MSA | DMSO | 82 | Humins 18 |
| 4 (according to the invention) | Glucose + Fructose | MSA | DMSO | 76 | Humins 24 |
| 5 (not according to the invention) | Fructose | — | NMP | <1 | Humins 40 |
| 6 (not according to the invention) | Fructose | — | DMSO | 65 | Humins 35 |
| 7 (not according to the invention) | Fructose | Amberlyst 15 | NMP | 45 | Humins 55 |
| 8 (not according to the invention) | Fructose | MSA | Ethanol | 17 | Ethyl levulinate 7 Ethoxymethyl-furfural 5 Humins 37 |

The reaction kinetics are quicker and the yield of 5-HMF is greater in the case using catalysts of the family of the homogeneous sulphonic acids such as methanesulphonic acid in an aprotic polar solvent according to the invention compared with the absence of catalysts in an aprotic polar solvent and compared with the use of a catalyst of the family of the heterogeneous sulphonic acids such as Amberlyst 15 in an aprotic polar solvent and compared with the use of catalysts of the family of the homogeneous sulphonic acids such as methanesulphonic acid in a protic polar solvent such as ethanol.

The yield of unwanted products is less in the case using catalysts of the family of the homogeneous sulphonic acids such as methanesulphonic acid in an aprotic polar solvent according to the invention compared with the absence of catalysts in an aprotic polar solvent and compared with the use of a catalyst of the family of the heterogeneous sulphonic acids such as Amberlyst 15 in an aprotic polar solvent and compared with the use of catalysts of the family of the homogeneous sulphonic acids such as methanesulphonic acid in a protic polar solvent such as ethanol.

Thus, it unexpectedly appears that is it highly advantageous to use catalysts of the family of the homogeneous sulphonic acids in an aprotic polar solvent according to the invention for the conversion of sugars to 5-HMF.

The invention claimed is:

1. A process comprising producing 5-hydroxymethylfurfural by contacting a feedstock comprising at least one sugar with one or more homogeneous sulphonic acid catalysts in the presence of at least one aprotic polar solvent having a dipole moment expressed in Debye (D) greater than 2.00, the aprotic polar solvent being pyridine, butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulpholane, N-methylpyrrolidone, dimethyl sulphoxide, propylene carbonate or γ-valerolactone, used alone or in a mixture, at a temperature of 30° C. to 200° C., and at a pressure of 0.1 MPa to 10 MPa in which said catalysts have formula

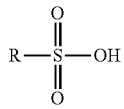

in which R is
halogen,
linear or branched, cyclic or non-cyclic alkyl, of 1 to 20 carbon atoms optionally substituted with at least one substituent that is:
an oxo group,
halogen or
an aryl group, optionally fused, optionally substituted by halogen and/or linear or branched, cyclic or non-cyclic alkyl groups of 1 to 20 carbon atoms,
aryl of 6 to 14 carbon atoms optionally substituted with at least one substituent that is:
linear or branched, cyclic or non-cyclic alkyl of 1 to 20 carbon atoms optionally substituted with at least one halogen or at least one nitro group,
halogen or
a nitro group.

2. The process according to claim 1 in which said sugar is an oligosaccharide or monosaccharide, alone or in a mixture.

3. The process according to claim 2 in which the monosaccharide is glucose, mannose or fructose, used alone or in a mixture.

4. The process according to claim 2 in which the oligosaccharide is saccharose, lactose, maltose, isomaltose, inulobiose, melibiose, gentiobiose, trehalose, cellobiose, cellotriose, cellotetraose or an oligosaccharide originating from hydrolysis of a polysaccharide originating from the hydrolysis of starch, inulin, cellulose or hemicellulose, used alone or in a mixture.

5. The process according to claim 1, in which R is a linear alkyl group containing from 1 to 6 carbon atoms.

6. The process according to claim 5, in which R is a methyl group and the homogeneous sulphonic catalyst is methanesulphonic acid.

7. The process according to claim 1, in which R is a branched alkyl group containing 3 to 10 carbon atoms.

8. Process according to claim 1, in which R is a substituted aryl group and the catalyst of the family of the sulphonic acids is p-toluenesulphonic acid.

9. The process according to claim 1, in which the aprotic polar solvent is acetone, N,N-dimethylformamide, N,N-dimethylacetamide, sulpholane, N-methylpyrrolidone, dimethyl sulphoxide, propylene carbonate and γ-valerolactone alone or in a mixture.

10. The process according to claim 1, in which the temperature is 50° C. to 200° C., and in which the pressure is 0.1 MPa to 8 MPa.

11. The process according to claim 1, in which the feedstock is introduced at a solvent/feedstock mass ratio of 0.1 to 200.

12. The process according to claim 1, in which the homogeneous sulphonic acid catalyst is introduced at a feedstock/organic catalyst(s) mass ratio of 1 to 1000.

\* \* \* \* \*